United States Patent
Maj et al.

(10) Patent No.: US 9,758,479 B2
(45) Date of Patent: Sep. 12, 2017

(54) METHOD FOR PREPARING ORGANIC PEROXIDES

(71) Applicant: ARKEMA FRANCE, Colombes (FR)

(72) Inventors: Philippe Maj, Brignais (FR); Serge Hub, Villeurbanne (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/910,937

(22) PCT Filed: Jul. 9, 2014

(86) PCT No.: PCT/FR2014/051764
§ 371 (c)(1),
(2) Date: Feb. 8, 2016

(87) PCT Pub. No.: WO2015/018996
PCT Pub. Date: Feb. 12, 2015

(65) Prior Publication Data
US 2016/0207882 A1   Jul. 21, 2016

(30) Foreign Application Priority Data

Aug. 8, 2013 (FR) ...................... 13 57893

(51) Int. Cl.
| | | |
|---|---|---|
| *C07C 409/16* | (2006.01) | |
| *C07C 407/00* | (2006.01) | |
| *B01J 27/053* | (2006.01) | |
| *B01J 31/02* | (2006.01) | |

(52) U.S. Cl.
CPC ........... *C07C 409/16* (2013.01); *B01J 27/053* (2013.01); *B01J 31/0225* (2013.01); *C07C 407/00* (2013.01); *C07C 407/003* (2013.01)

(58) Field of Classification Search
CPC ............................. C07C 409/16; C07C 407/00
See application file for complete search history.

(56) References Cited

U.S. PATENT DOCUMENTS

| 2,668,180 | A |   | 2/1954  | Boardman |
|---|---|---|---|---|
| 3,764,628 | A |   | 10/1973 | Gregorian et al. |
| 3,833,664 | A | * | 9/1974  | Aoshima ............... C07C 409/16 568/578 |
| 3,919,326 | A |   | 11/1975 | Gregory |
| 5,981,805 | A | * | 11/1999 | Nelson ................. C07C 409/16 252/182.23 |
| 6,107,385 | A |   | 8/2000  | Imahashi |
| 6,303,681 | B1 |  | 10/2001 | Furukawa et al. |

FOREIGN PATENT DOCUMENTS

| EP | 0 953 599 A1 | 11/1999 |
|---|---|---|
| EP | 1 092 751 A1 | 4/2001 |
| FR | 2 870 542 A1 | 11/2005 |
| FR | 2 985 731 A1 | 7/2013 |
| SU |   504 762 A1 | 2/1976 |

OTHER PUBLICATIONS

International Search Report (PCT/ISA/210) mailed on Sep. 29, 2014, by the European Patent Office as the International Searching Authority for International Application No. PCT/FR2014/051764.
Written Opinion (PCT/ISA/237) mailed on Sep. 29, 2014, by the European Patent Office as the International Searching Authority for International Application No. PCT/FR2014/051764.

\* cited by examiner

*Primary Examiner* — Medhanit Bahta
(74) *Attorney, Agent, or Firm* — Buchanan Ingersoll & Rooney P.C.

(57) ABSTRACT

A method for preparing peroxide, including a step of treating, in a reaction medium, a component having at least one tertiary alcohol grouping with a compound having at least one tertiary hydroperoxide function in the presence of a catalyst, said method being characterized in that the catalyst includes a sulphonic acid and a inorganic acid, the molar ratio between the sulphonic acid and the aforementioned component including at least one tertiary alcohol grouping ranges from 0.05 to 0.8, and the molar ratio between the inorganic acid and the aforementioned component including at least one tertiary alcohol grouping ranges from 0.05 to 0.8. Also, to the peroxide resulting directly from said preparation method.

15 Claims, No Drawings

METHOD FOR PREPARING ORGANIC PEROXIDES

FIELD OF THE INVENTION

The invention relates to a process for preparing/manufacturing/producing tertiary alkyl organic peroxides via a condensation reaction between compounds containing at least one tertiary alcohol group and a compound containing at least one tertiary hydroperoxide function in the presence of a catalyst.

The chemical structure of peroxides is characterized by the presence of two oxygen molecules linked together via a covalent single bond. This structure is intrinsically unstable. Peroxides readily decompose into extremely reactive free radicals.

Organic peroxides are very widely used in the chemical industry and also in the plastics and rubber sectors. They intervene as initiators in the radical polymerization of monomers into thermoplastic polymers, as hardeners for thermosetting polyester resins and as crosslinking agents for elastomers and polyethylene. Organic peroxides serve as a source of free radicals in many organic syntheses.

The present manufacturing/production process applies in particular to the synthesis of organic peroxides having the following general formulae:

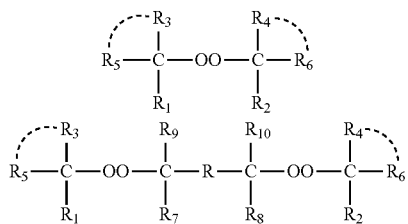

in which $R_1$ and $R_2$ are optionally substituted alkyl or aryl groups (alkyl, alkenyl, etc.), $R_3$ to $R_{10}$ are alkyl groups containing from 1 to 3 carbon atoms which may be linked together to form a ring (cyclopentyl, cyclohexyl, etc.), R is a substituted or unsubstituted aryl group, or an alkyl group containing from 1 to 4 carbon atoms which may contain unsaturations (alkenyl or alkynyl groups).

PRIOR ART

One of the industrially used routes for synthesizing alkyl organic peroxide via acid catalysis requires a large amount of condensation agent(s) such as sulfuric acid. The use of a large amount of sulfuric acid entails a high cost for the treatment of the aqueous phases due to the large amounts of sulfate generated in the effluents.

This synthetic process is disclosed, for example, in GB 1 049 989. An aqueous 62.5% sulfuric acid solution is used as catalyst and represents 49% by weight of the preparation.

Moreover, a synthetic process requiring a high concentration of sulfuric acid presents a serious industrial risk. The higher the concentration of acid, the more the temperature must be rigorously maintained at low temperatures. In order to control the reaction, this type of process requires temperature conditions generally below 10° C. The higher the concentration of acid, the more the peroxide synthesis requires a low temperature in the reaction medium, typically less than or equal to 5° C. In order to obtain a high yield, this synthetic route requires a high concentration of acid, but then the costs associated with the required cooling become prohibitive.

In addition to the costs associated with cooling, the drawback of a relatively low yield and the production of large amounts of sulfates in the effluents, this process produces an appreciable amount of phenolic-type byproducts which foul the reactor. The reactor thus requires regular cleaning, which slows down the production and represents a substantial additional cost.

The reason for the large amounts of acid required for this synthetic route is in particular because of the water formed during the condensation reaction, which very significantly dilutes the catalytic effect of the acidic condensation agents.

An alternative method to the process comprising a high concentration of sulfuric acid consists in removing the water formed, in the presence of an organic solvent, by azeotropic distillation under reduced pressure. Amounts of less than 1% of acidic condensation agent may thus be used.

U.S. Pat. No. 3,919,326 discloses a process for preparing organic peroxides in the presence of less than 1% of para-toluenesulfonic acid. The water formed during the condensation reaction is removed gradually as the reaction proceeds, with the organic solvent, by azeotropic distillation, under reduced pressure.

This process limits the amount of acid salts generated in the effluents, but requires the use of special equipment for the extraction under vacuum of the water formed, thus limiting its uses.

Processes not using a large amount of condensation agent or not requiring vacuum extraction conditions have been proposed, such as those disclosed in U.S. Pat. No. 2,668,180 and FR 2 379 518.

U.S. Pat. No. 2,668,180 discloses a process for producing organic peroxides at atmospheric pressure, at high temperature (80-115° C.) in the presence of a relatively low amount of acidic condensation agent as catalyst. The acidic condensation agents used are para-toluenesulfonic acid, sulfuric acid and boron trifluoride etherate. The yields of peroxides obtained are unsatisfactory. Furthermore, the high temperatures used may induce spurious thermal decomposition reactions of the peroxides.

FR 2 379 518 discloses a process for obtaining organic peroxide in the presence of an aqueous solution of mineral acids such as hydrochloric acid and nitric acid. The peroxides thus produced precipitate massively in the reaction medium and are separated out by filtration or decantation.

These processes do not give satisfactory yields and the production of substantial precipitates during the synthesis greatly complicates the manufacturing process, which especially entails major economic drawbacks.

EP 0 967 194 is moreover known, which discloses a process for obtaining peroxide in the presence of sulfonic acid as catalyst at a temperature above 40° C. at atmospheric pressure. The catalyst is added gradually over a period of one hour so as to limit any exothermicity. A minimum yield of 70% to 80% is obtained after two hours of reaction.

In said process, it should be noted that the solvent used is cumene and not an alkane. Furthermore, said process does not envisage adding a mineral acid and the condensation reactions are relatively slow. Finally, the spurious reactions, such as the dehydration of the alcohol or the formation of phenol, are substantial.

Patent SU 504 762, published in 1976, is known, which discloses a process for preparing 1,4-bis-[2-(tert-butylperoxy)isopropyl]benzene via a condensation reaction of tert-butyl hydroperoxide and 1,4-bis-[2-hydroxyisopropyl]benzene in the presence of sulfuric acid and acetic anhydride.

Finally, U.S. Pat. No. 3,764,628 is known, which discloses a process for preparing bis(alkylperoxyalkyl)benzene derivatives by reaction of a bishydroxyalkylbenzene and a tertiary hydroperoxide in the presence of sulfuric acid as catalyst.

There is thus a great need to obtain an industrial process for producing organic peroxide that does not have the drawbacks of the prior art.

BRIEF DESCRIPTION OF THE INVENTION

After various experiments and operations, the Applicant has discovered, surprisingly, that, contrary to the teachings that are well known to those skilled in the art, the simultaneous use of an amount of sulfonic acid and of mineral acid in given proportions makes it possible to perform the reaction for producing organic peroxide under conditions that are readily achievable industrially, without the need to remove the water formed throughout the reaction, while at the same time obtaining high yields. Furthermore, the process according to the invention does not generate any byproducts, or only negligible amounts, more particularly of phenolic type when the reagents are aromatic (at least the component bearing the alcohol function contains an aromatic function, or even the compound comprising the hydroperoxide function). These byproducts reduce the yield of desired product, decrease the final purity of the product and may be the cause of fouling of the reactor (phenolic byproducts).

Thus, the present invention relates to a process for preparing peroxide, comprising a step of placing in contact in a reaction medium a component containing at least one tertiary alcohol group with a compound containing at least one tertiary hydroperoxide function in the presence of a catalyst, characterized in that the catalyst comprises a sulfonic acid and a mineral acid, the mole ratio between the sulfonic acid and said component comprising at least one tertiary alcohol group is between 0.05 and 0.8, and the mole ratio between the mineral acid and said component comprising at least one tertiary alcohol group is between 0.05 and 0.8.

No prior art document discloses the use of a mixture of mineral acid and of sulfonic acid at atmospheric pressure for the preparation/manufacture/production of peroxides. Furthermore, from his general knowledge, for safety reasons, a person skilled in the art is not led to consider the use of a peroxide production process comprising a relatively concentrated mineral acid, such as sulfuric acid, at temperatures above room temperature. The mixture of mineral acid and sulfonic acid makes it possible to work at temperatures above room temperature without creating any safety risk(s).

The invention especially has the following advantages:
  using standard industrial conditions (without the need for complex and expensive equipment), simply requiring atmospheric pressure and a temperature slightly above room temperature,
  not requiring removal of the water formed throughout the reaction,
  using a smaller amount of acid than in the case of using mineral acids alone, and thus making it possible, in the case of sulfuric acid, to limit the amount of sulfate expelled in the effluents,
  obtaining a high yield of organic peroxide in particular due to a synergistic effect of the kinetics relative to that for the acids taken separately,
  reducing the catalyst introduction time relative to the process using a large amount of mineral acid alone.

Other advantageous features of the invention are specified hereinbelow:
Advantageously, the mole ratio between the sulfonic acid and the component comprising at least one tertiary alkyl group is between 0.1 and 0.6, preferably between 0.1 and 0.3.
Advantageously, the mole ratio between the mineral acid and the component comprising at least one tertiary alcohol group is between 0.1 and 0.6, preferably between 0.1 and 0.5.
According to a particularly advantageous aspect of the invention, the process is performed at atmospheric pressure (±0.2 bar).
According to a preferred embodiment of the invention, said component and/or said compound comprises one or more aromatic functions such that the peroxide comprises at least one aromatic function.
According to a possibility offered by the invention, said compound comprising a hydroperoxide group is chosen from tert-butyl hydroperoxide, tert-amyl hydroperoxide, 1-methylcyclohexyl hydroperoxide and 1-methylcyclopentyl hydroperoxide, preferably tert-butyl hydroperoxide.
According to another possibility offered by the invention, said compound comprising a hydroperoxide group is chosen from 2,5-dimethyl-2,5dihydroperoxy-3-hexyne and 2,5-dimethyl-2,5-dihydroperoxyhexane.
According to one embodiment of the invention, said component comprising an alcohol group is chosen from tert-butanol, tert-amyl alcohol, cumyl alcohol, 1-methylcyclohexanol and 1-methylcyclopentanol, preferably cumyl alcohol.
According to another embodiment of the invention, said component comprising an alcohol group is chosen from α,α'-dihydroxydiisopropylbenzene, 2,5-dimethyl-2,5-dihydroxy-3-hexyne and 2,5-dimethyl-2,5-dihydroxyhexane, and more preferably α,α'-dihydroxydiisopropylbenzene.
The sulfonic acid is preferably chosen from alkyl or aryl sulfonic acids, more particularly aryl sulfonic acids such as benzenesulfonic acid, para-toluenesulfonic acid, naphthalenesulfonic acid, xylenesulfonic acid, cumenesulfonic acid, and mixtures thereof, and preferably chosen from cumenesulfonic acid and para-toluenesulfonic acid.
As regards the mineral acid, it is preferably chosen from sulfuric acid, hydrochloric acid, nitric acid, phosphoric acid and perchloric acid, and mixtures thereof, preferably chosen from sulfuric acid.
Preferably, the stoichiometric excess between the reagents, namely between said compound comprising at least one tertiary hydroperoxide group and said component containing at least one tertiary alcohol function, is between 0.01 and 1, preferably between 0.05 and 0.5 and more preferably between 0.1 and 0.3.
The stoichiometric excess is referred to herein because the ratio of hydroperoxide to alcohol must respectively be at least 1 (mol) to 1 (mol) for a monoperoxide and 2 (mol) to 1 (mol) for a diperoxide. Thus, for example, in the case of preparation of a mixture of the meta and para isomers of α,α'-bis(tert-butylperoxy)diisopropylbenzene, the process will be performed with an excess of hydroperoxide relative to the diol. However, this stoichiometric excess may also be in favour of the alcohol rather than of the hydroperoxide, for example in the case of preparation of 2,5-bis(1-methylcyclohexylperoxy)-2,5-dimethyl-3-hexyne.

Advantageously, the step of placing in contact is performed at a temperature of between 10° C. and 60° C., preferably between 20° C. and 50° C.

According to one aspect of the invention, the process may comprise a step prior to said step of placing in contact in the reaction medium, consisting of a step of mixing the mineral acid with the sulfonic acid outside said reaction medium.

According to a preferred embodiment of the invention, the catalyst consists solely of the sulfonic acid and the mineral acid.

The invention also relates to the peroxide obtained directly via the preparation process defined above. Such a peroxide has the advantageous feature of being virtually pure on conclusion of its preparation, such that it does not require any washing intended to remove impurities therefrom. In certain cases, when a level of purity (absence of traces of byproducts, in particular of acids) is desired, it may nevertheless be desirable to perform one or even two washes of the peroxide. Thus, the peroxide obtained via the process according to the invention differs from the peroxides of the prior art in that, once obtained, it comprises only a very small amount of impurity, in particular of acid (liable to be detrimental to the future applications of the peroxide), typically less than 50 ppm (parts per million), or even preferably less than 20 ppm.

Thus, the peroxide obtained via the preparation process according to the invention comprises less than 50 ppm of acid, preferably less than 20 ppm.

Other advantages may arise upon reading the following description. The following description is given solely by way of nonlimiting illustration.

DETAILED DESCRIPTION OF THE INVENTION

The invention relates to a process for producing peroxide, comprising a step of placing a compound comprising at least one tertiary alcohol group in contact with a compound containing at least one tertiary hydroperoxide function in the presence of a catalyst. The compound comprising at least one tertiary alcohol group reacts by condensation with a compound containing at least one tertiary hydroperoxide function via acid catalysis.

The peroxides produced according to the process of the invention are dialkyl peroxides that may contain up to two O—O (oxygen-oxygen) peroxide functions.

As regards the compounds comprising at least one tertiary alcohol group, they may be tert-butyl alcohol, tert-amyl alcohol, cumyl alcohol, 1-methylcyclohexanol, 1-methylcyclopentanol, α,α'-dihydroxydiisopropylbenzene, 2,5-dimethyl-3-hexyne-2,5diol or 2,5-dimethyl-2,5-hexanediol.

As regards the compound containing at least one tertiary hydroperoxide function, it may be tert-butyl hydroperoxide, tert-amyl hydroperoxide, 1-methylcyclohexyl hydroperoxide, 1-methylcyclopentyl hydroperoxide, 2,5-dimethyl-2,5dihydroperoxy-3-hexyne or 2,5-dimethyl-2,5-dihydroperoxyhexane.

The process for producing organic dialkyl peroxide according to the invention is performed by placing an alcohol in contact with a hydroperoxide in the presence of a catalyst.

The process according to the invention comprises the use of a catalyst comprising a combination of a mineral acid and a sulfonic acid. Only these two components (mineral and sulfonic acids) are required to perform the invention (to solve the technical problems), but it may optionally be envisaged to combine other components to constitute the catalyst.

As regards the mineral acids, they may be sulfuric acid, hydrochloric acid, perchloric acid, nitric acid or phosphoric acid, and mixtures thereof.

As regards the sulfonic acids, they may be alkyl sulfonic acids such as methanesulfonic acid, fluoroalkyl sulfonic acids such as trifluoromethanesulfonic acid, aromatic sulfonic acids such as benzenesulfonic acid, para-toluenesulfonic acid, para-phenolsulfonic acid, naphthalenesulfonic acid, xylenesulfonic acid or cumenesulfonic acid, and mixtures thereof.

The mineral acid and the sulfonic acid according to the process of the invention may be added separately or may be premixed before introduction into the reaction medium.

The process according to the invention is preferably performed in the presence of an organic solvent. Solvents that may be mentioned include pentane, hexane, heptane, benzene, toluene, xylenes, cumene and chlorinated hydrocarbons.

| Peroxide | formula | Hydroperoxide | formula | Alcohol |
|---|---|---|---|---|
| Di-tert-butyl peroxide | (CH3)3C-OO-C(CH3)3 | tert-Butyl hydroperoxide | (CH3)3C-OOH | tert-Butanol |
| Di-tert-amyl peroxide | (tert-amyl)-OO-(tert-amyl) | tert-Amyl hydroperoxide | (tert-amyl)-OOH | tert-Amyl alcohol |
| tert-Butyl cumyl peroxide | cumyl-OO-C(CH3)3 | tert-Butyl hydroperoxide | (CH3)3C-OOH | Cumyl alcohol |
| Dicumyl peroxide | cumyl-OO-cumyl | Cumyl hydroperoxide | cumyl-OOH | Cumyl alcohol |
| tert-Amyl cumyl peroxide | cumyl-OO-(tert-amyl) | tert-Amyl hydroperoxide | (tert-amyl)-OOH | Cumyl alcohol |
| Bis-(1-methylcyclopentyl) peroxide | (1-methylcyclopentyl)-OO-(1-methylcyclopentyl) | 1-Methylcyclopentyl hydroperoxide | (1-methylcyclopentyl)-OOH | 1-Methylcyclopentanol |

-continued

| Peroxide | formula | Hydroperoxide | formula | Alcohol | formula |
|---|---|---|---|---|---|
| α,α'-Bis(tert-butylperoxy)diisopropylbenzene | (structure) | tert-Butyl hydroperoxide | (structure) | α,α'-Dihydroxydiisopropylbenzene optional mixture of isomers | (structure) |
| 2,5-Bis(tert-butylperoxy)-2,5-dimethylhexane | (structure) | 2,5-Dimethyl-2,5-dihydroperoxyhexane | (structure) | tert-Butanol | (structure) |
| 2,5-Bis(tert-butylperoxy)-2,5-dimethyl-3-hexyne | (structure) | 2,5-Dimethyl-2,5-dihydroperoxy-3-hexyne | (structure) | tert-Butanol | (structure) |
| 2,5-Bis(1-methylcyclopentylperoxy)-2,5-dimethyl-3-hexyne | (structure) | 2,5-Dimethyl-2,5-dihydroperoxy-3-hexyne | (structure) | 1-Methylcyclopentanol | (structure) |

The process according to the invention does not require removal, azeotropically or by other means, of the water formed by the condensation reaction gradually as the peroxide production reaction proceeds.

Once the peroxide has been obtained, at least a final step of removal of the aqueous phase after decantation is conventionally envisaged, along with steps well known to those skilled in the art, such as steps of basic neutralization of the catalyst, aqueous washing, removal of the reaction solvent and purification.

Examples of implementation of the preparation process according to the invention are presented hereinbelow. These examples are illustrated with the production of the mixture of meta and para isomers of α,α'-bis(tert-butylperoxy)diisopropylbenzene.

However, experiments were conducted on all the peroxides listed in this table.

It emerges that the production of peroxides comprising at least one aromatic nucleus is particularly suited to the preparation process according to the invention (at least one of the reagents, conventionally the component bearing the alcohol function, comprising an aromatic nucleus).

However, the production of aliphatic peroxides, including peroxides comprising saturated rings, is also advantageously performed via the preparation process according to the invention and makes it possible to solve virtually all, or even all, of the technical problems encountered with the preparation processes of the prior art.

Example 1 (According to the Invention): Implementation of the Synthetic Process According to the Invention 66.5 grams (g) of a tert-butyl hydroperoxide (TBHP) solution at 40.5 wt % (the term "wt %" means the "weight percent") in heptane and 27.8 g of a mixture of isomers (meta/para) of α,α'-dihydroxy-diisopropylbenzene at 93 wt % (diol) are placed in a 250 milliliter (ml) reactor equipped with a bottom valve, a stirrer, a temperature probe and a reflux condenser. The mixture is heated to 30° C. while stirring under nitrogen. At this temperature, 8.6 g of a cumylsulfonic acid solution (65 wt %) are added in a single injection. 8 grams (g) of a sulfuric acid solution (70 wt %) are then gradually added over about two (2) minutes. The temperature of the medium rises to 37-40° C. When the addition of the acids is complete, the temperature is maintained at 40° C. for a time of 115 min (minutes) while stirring the medium.

After this period, the stirring is stopped while maintaining the reactor at 40° C. Two phases separate on settling. The lower phase (aqueous—25.6 g) is removed from the reactor via the bottom valve.

While resuming the stirring, the upper phase (organic) is washed at 40° C. with 63.2 g of water. After (5) minutes of washing, the stirring is stopped to separate two phases. The lower phase (aqueous—63.8 g) is removed via the bottom valve.

While resuming the stirring, the upper phase (organic) is washed at 40° C. with 62.4 g of aqueous sodium hydroxide solution (15 wt %). After 5 minutes of washing, the stirring is stopped to separate two phases. The lower phase (aqueous—64.2 g) is removed via the bottom valve.

The process is completed with a final wash at 40° C. of the upper phase (organic) with 60.7 g of water. After 5 min of washing, the stirring is stopped to separate two phases. A lower phase (aqueous: 61.2 g) and an upper phase (organic: 77.3 g) are recovered.

After analysis, the organic solution contains 41.2 g of α,α'-bis(tert-butylperoxy)diisopropylbenzene ($C_{20}H_{34}O_4$), 0.35 g of α-(tert-butylperoxy)-α'-hydroxyisopropylbenzene ($C_{16}H_{26}O_3$) and 0.43 g of α-(tert-butylperoxy)-α'-isopropenylbenzene ($C_{16}H_{24}O_2$) corresponding, respectively, to the sum of the meta and para isomers of each of the compounds. This represents a yield of α,α'-bis(tert-butylperoxy)diisopropylbenzene of 92% relative to the diol engaged. The material balance on these three aromatic products is 93% relative to the diol engaged.

Example 1bis

The process is performed in the same manner as in Example 1, but using cumyl alcohol as tertiary alcohol and the operating conditions described in the table below.

| Example | | 1bis |
|---|---|---|
| Sulfonic acid | | CUSA |
| Temperature | ° C. | 30 |
| Reaction time | min | 30 |
| TBHP/cumyl alcohol ratio | mol | 1.2 |
| [Sulfonic acid] | Weight % | 65 |
| [$H_2SO_4$] | Weight % | 70 |
| Sulfonic acid/cumyl alcohol ratio | mol | 0.1 |
| $H_2SO_4$/diol ratio | mol | 0.19 |
| Aromatic balance | mol % | 97 |
| tert-Butylcumyl peroxide yield | mol % | 96.6 |

Example 1ter

The process is performed in the same manner as in Example 1, but using cumyl alcohol as tertiary alcohol, cumyl hydroperoxide as tertiary hydroperoxide and cumene as solvent, and the operating conditions described in the table below.

| Example | | 1ter |
|---|---|---|
| Sulfonic acid | | CUSA |
| Temperature | ° C. | 30 |
| Reaction time | Min | 30 |
| Cumyl hydroperoxide/cumyl alcohol ratio | Mol | 1.2 |
| [Sulfonic acid] | Weight % | 65 |
| [$H_2SO_4$] | Weight % | 70 |
| Sulfonic acid/cumyl alcohol ratio | mol | 0.1 |
| $H_2SO_4$/cumyl alcohol ratio | mol | 0.16 |
| Aromatic balance | mol % | 95 |
| Dicumyl peroxide yield | mol % | 82 |

Example 1 Quatro

The process is performed in the same manner as in Example 1, but using tert-amyl alcohol as tertiary alcohol, tert-amyl hydroperoxide as tertiary hydroperoxide and methanesulfonic acid (MSA), and the operating conditions described in the table below.

It will be noted here that this Example 1 quatro corresponds to the definition of the main claim (claim 1), but not to the dependent claims 2 and 3.

| Example | | 1 quatro |
|---|---|---|
| Sulfonic acid | | MSA |
| Temperature | ° C. | 30 |
| Reaction time | min | 120 |
| tert-Amyl hydroperoxide/tert-amyl alcohol ratio | Mol | 1.1 |

-continued

| Example | | 1 quatro |
|---|---|---|
| [Sulfonic acid] | Weight % | 68 |
| [$H_2SO_4$] | Weight % | 70 |
| Sulfonic acid/tert-amyl alcohol ratio | mol | 0.37 |
| $H_2SO_4$/tert-amyl alcohol ratio | mol | 0.75 |
| Di-tert-amyl peroxide yield | mol % | 75 |

Counter-Examples 2 and 3

The process is performed in the same manner as in Example 1, but using each of the two acids separately.

| Counter-examples | | 2 | 3 |
|---|---|---|---|
| Acid | | CUSA | $H_2SO_4$ |
| Temperature | ° C. | 40 | 40 |
| Reaction time | min | 120 | 120 |
| TBHP/diol ratio | mol | 2.2 | 2.3 |
| [acid] | Weight % | 65 | 70 |
| Acid/diol ratio | mol | 0.21 | 0.32 |
| Aromatic balance | mol | 97 | 86 |
| $C_{20}H_{34}O_4$ yield | mol | 58.3 | 8.4 |

It is found that the use of only one acid, whether a sulfonic acid or a mineral acid, in the proportions described in Example 1, does not make it possible to achieve the same yield of peroxide desired and remains much lower than that obtained by combining the two acids.

Combining the two acids also leads to a better result (in terms of yield) than the sum of the results obtained by using each acid in isolation, thus reflecting a synergistic effect of the two acids.

It may be noted that the material balance of the aromatic species degrades on using sulfuric acid alone under the conditions mentioned. This phenomenon is not observed on combining a sulfonic acid, which also constitutes one of the advantages of this invention.

Counter-Examples 2bis and 3bis

The process is performed in the same manner as in Example 1bis, but using each of the two acids separately.

| Counter-examples | | 2 bis | 3 bis |
|---|---|---|---|
| Acid | | CUSA | $H_2SO_4$ |
| Temperature | ° C. | 30 | 30 |
| Reaction time | min | 30 | 30 |
| TBHP/cumyl alcohol ratio | mol | 1.2 | 1.2 |
| [acid] | Weight % | 65 | 70 |
| Acid/cumyl alcohol ratio | mol | 0.1 | 0.19 |
| Aromatic balance | Mol % | 98 | 86 |
| tert-Butylcumyl peroxide yield | Mol % | 34.4 | 41.3 |

Counter-Examples 2ter and 3ter

The process is performed in the same manner as in Example 1ter, but using each of the two acids separately.

| Counter-examples | | 1ter | 1ter |
|---|---|---|---|
| Acid | | CUSA | $H_2SO_4$ |
| Temperature | ° C. | 30 | 30 |
| Reaction time | g/min | 30 | 30 |
| Cumyl hydroperoxide/cumyl alcohol ratio | mol | 1.2 | 1.2 |
| [acid] | Weight % | 65 | 70 |
| Acid/cumyl alcohol ratio | mol | 0.1 | 0.2 |
| Aromatic balance | Mol % | 95 | 87 |
| Dicumyl peroxide yield | Mol % | 32 | 31 |

Counter-Examples 2quatro and 3quatro

The process is performed in the same manner as in Example 1quatro, but using each of the two acids separately.

| Counter-examples | | 2 quatro | 3quatro |
|---|---|---|---|
| Acid | | MSA | $H_2SO_4$ |
| Temperature | ° C. | 30 | 30 |
| Reaction time | min | 120 | 120 |
| tert-Amyl hydroperoxide/tert-amyl alcohol ratio | mol | 1.2 | 1.2 |
| [acid] | Weight % | 68 | 68 |
| Acid/tert-amyl alcohol ratio | mol | 0.39 | 0.73 |
| Di-tert-amyl peroxide yield | Mol % | 3.7 | 23.5 |

Examples 4 to 6 (According to the Invention)

The process is performed in the same manner as in Example 1, but changing the nature of the sulfonic acid used: para-toluenesulfonic acid (PTSA), benzenesulfonic acid (BSA), phenolsulfonic acid (PPSA).

| Example | | 4 | 5 | 6 |
|---|---|---|---|---|
| Sulfonic acid | | PTSA | BSA | PPSA |
| Temperature | ° C. | 40 | 40 | 40 |
| Reaction time | min | 120 | 120 | 120 |
| TBHP/diol ratio | mol | 2.2 | 2.3 | 2.3 |
| [Sulfonic acid] | Weight % | 70 | 70 | 65 |
| [$H_2SO_4$] | Weight % | 70 | 70 | 70 |
| Sulfonic acid/diol ratio | mol | 0.209 | 0.209 | 0.213 |
| $H_2SO_4$/diol ratio | mol | 0.498 | 0.433 | 0.433 |
| Aromatic balance | mol % | 97.7 | 95.4 | 100.3 |
| $C_{20}H_{34}O_4$ yield | mol | 89.3 | 87.5 | 76.9 |

The use of the mixture of sulfonic acid with sulfuric acid according to the invention makes it possible to achieve yields of α,α'-bis(tert-butylperoxy)diisopropylbenzene of greater than or equal to 75% in not more than two hours of reaction.

Counter-Example 7

The process is performed in the same manner as in the preceding example, but using PTSA alone, not in combination with sulfuric acid.

| Counter-examples | | 7 |
|---|---|---|
| Acid | | PTSA |
| Temperature | ° C. | 40 |
| Reaction time | min | 120 |
| TBHP/diol ratio | mol | 2.2 |
| [acid] | Weight % | 65 |
| Acid/diol ratio | mol | 0.21 |

-continued

| Counter-examples | | 7 |
|---|---|---|
| Aromatic balance | mol | 98 |
| $C_{20}H_{34}O_4$ yield | mol | 41.7 |

It is found that the use of the sulfonic acid alone, in the proportions described, does not lead to a satisfactory yield (<75%).

Examples 8 to 16 (According to the Invention)

The process is performed in the same manner as in Example 1, but changing the reaction parameters (ratios, concentrations).

| | | Example | | | | | | | | |
|---|---|---|---|---|---|---|---|---|---|---|
| | | 8 | 9 | 10 | 11 | 12 | 13 | 14 | 15 | 16 |
| Sulfonic acid | | CUSA | CUSA | CUSA | CUSA | CUSA | CUSA | CUSA | CUSA | CUSA |
| Temperature | ° C. | 40 | 40 | 40 | 40 | 40 | 40 | 40 | 30 | 50 |
| Reaction time | min | 94 | 90 | 111 | 120 | 150 | 120 | 90 | 120 | 129 |
| TBHP/diol ratio | mol | 2.2 | 2.4 | 2.2 | 2.2 | 2.4 | 2.2 | 2.2 | 2.4 | 2.4 |
| [Sulfonic acid] | Weight % | 65 | 65 | 65 | 65 | 65 | 65 | 65 | 65 | 65 |
| [$H_2SO_4$] | Weight % | 96 | 96 | 80 | 70 | 70 | 70 | 70 | 96 | 96 |
| Sulfuric acid/diol ratio | mol | 0.129 | 0.17 | 0.127 | 0.21 | 0.126 | 0.17 | 0.128 | 0.169 | 0.137 |
| $H_2SO_4$/diol ratio | mol | 0.345 | 0.346 | 0.344 | 0.428 | 0.348 | 0.345 | 0.346 | 0.345 | 0.136 |
| Aromatic balance | mol | 97.6 | 97.2 | 94.8 | 98.3 | 101 | 95.8 | 90.3 | 96.9 | 90.8 |
| $C_{20}H_{34}O_4$ yield | mol | 87.4 | 89.7 | 85.6 | 91.6 | 93.6 | 88.9 | 84.3 | 89.4 | 59.8 |

High yields of the desired peroxide are found in all the tests performed.

The synergistic effect is found by comparing the results obtained with those of Counter-examples 17 to 19 performed with only one acid.

| Counter-examples | | 17 | 18 | 19 |
|---|---|---|---|---|
| Sulfonic acid | | CUSA | CUSA | CUSA |
| Temperature | ° C. | 40 | 40 | 40 |
| Reaction time | min | 120 | 120 | 120 |
| TBHP/diol ratio | mol | 2.2 | 2.4 | 2.2 |
| [Sulfonic acid] | Weight % | 65 | 65 | 65 |
| Sulfonic acid/diol ratio | mol | 0.13 | 0.17 | 0.21 |
| Aromatic balance | mol | | | |
| $C_{20}H_{34}O_4$ yield | mol | 41.8 | 50.7 | 58.3 |

The invention claimed is:

1. A process for preparing peroxide, comprising a step of placing in contact in a reaction medium a component containing at least one tertiary alcohol group with a compound containing at least one tertiary hydroperoxide function in the presence of a catalyst, wherein:
the catalyst comprises a sulfonic acid and a mineral acid,
the mole ratio between the sulfonic acid and said component comprising at least one tertiary alcohol group is between 0.05 and 0.8, and
the mole ratio between the mineral acid and said component comprising at least one tertiary alcohol group is between 0.05 and 0.8.

2. The process as claimed in claim 1, wherein the mole ratio between the sulfonic acid and the component comprising at least one tertiary alcohol group is between 0.1 and 0.6.

3. The process as claimed in claim 1 wherein the mole ratio between the mineral acid and the component comprising at least one tertiary alcohol group is between 0.1 and 0.6.

4. The process as claimed in claim 1, wherein the process is performed at atmospheric pressure (±0.2 bar).

5. The process as claimed in claim 1, wherein said component and/or said compound comprises one or more aromatic functions such that the peroxide comprises at least one aromatic function.

6. The process as claimed in claim 1, wherein said compound comprising a hydroperoxide group is selected from the group consisting of tert-butyl hydroperoxide, tert-amyl hydroperoxide, 1-methylcyclohexyl hydroperoxide and 1-methylcyclopentyl hydroperoxide.

7. The process as claimed in claim 1, wherein said compound comprising a hydroperoxide group is selected from the group consisting of 2,5-dimethyl-2,5-dihydroperoxy-3-hexyne and 2,5-dimethyl-2,5-dihydroperoxyhexane.

8. The process as claimed in claim 1, wherein said component comprising an alcohol group is selected from the group consisting of tert-butanol, tert-amyl alcohol, cumyl alcohol, 1-methylcyclohexanol and 1-methylcyclopentanol.

9. The process as claimed in claim 1, wherein said component comprising an alcohol group is selected from the group consisting of α,α'-dihydroxydiisopropylbenzene, 2,5-dimethyl-2,5-dihydroxy-3-hexyne and 2,5-dimethyl-2,5-dihydroxyhexane.

10. The process as claimed in claim 1, wherein the sulfonic acid is selected from the group consisting of alkyl sulfonic acid, aryl sulfonic acid, and mixtures thereof.

11. The process as claimed in claim 1, wherein the mineral acid is selected from the group consisting of sulfuric acid, hydrochloric acid, nitric acid, phosphoric acid and perchloric acid, and mixtures thereof.

12. The process as claimed in claim 1, wherein the stoichiometric excess between the reagents, namely between said compound comprising at least one tertiary hydroperoxide group and said compound containing at least one tertiary alcohol function, is between 0.01 and 1.

13. The process as claimed in claim 1, wherein the step of placing in contact is performed at a temperature of between 10° C. and 60° C.

14. The process as claimed in claim 1, wherein it comprises a step prior to said step of placing in contact in the reaction medium, consisting of a step of mixing the mineral acid with the sulfonic acid outside said reaction medium.

15. The process as claimed in claim 1, wherein the catalyst consists solely of the sulfonic acid and the mineral acid.

* * * * *